United States Patent [19]

Tojo et al.

[11] Patent Number: 4,661,639
[45] Date of Patent: Apr. 28, 1987

[54] PROCESS FOR PRODUCING CYCLIC ALCOHOL

[75] Inventors: Masahiro Tojo; Yohei Fukuoka, both of Okayama, Japan

[73] Assignee: Asahi Kasei Kogyo Kabushiki Kaisha, Osaka, Japan

[21] Appl. No.: 737,854

[22] Filed: May 28, 1985

[30] Foreign Application Priority Data

| May 25, 1984 [JP] | Japan | 59-104494 |
| May 25, 1984 [JP] | Japan | 59-104496 |
| May 25, 1984 [JP] | Japan | 59-104634 |
| May 28, 1984 [JP] | Japan | 59-106558 |

[51] Int. Cl.⁴ .............................................. C07C 35/06
[52] U.S. Cl. ..................................... 568/835; 568/832; 568/895
[58] Field of Search ................. 568/835, 832, 895, 897

[56] References Cited

U.S. PATENT DOCUMENTS

| 3,450,777 | 1/1969 | Mizutani et al. | 568/835 |
| 4,214,107 | 7/1980 | Chang | 568/897 |
| 4,306,101 | 12/1981 | Slaugh et al. | 568/899 |
| 4,339,604 | 7/1982 | van Geem et al. | 568/897 |
| 4,469,905 | 9/1984 | Inwood | 568/899 |
| 4,507,512 | 3/1985 | Okumura et al. | 568/897 |
| 4,528,409 | 7/1985 | Mitsui et al. | 568/835 |

FOREIGN PATENT DOCUMENTS

| 127486 | 12/1984 | European Pat. Off. | 568/897 |
| 8104 | 3/1968 | Japan | 568/835 |
| 16125 | 12/1968 | Japan | 568/835 |
| 124723 | 7/1983 | Japan | 568/897 |
| 194828 | 11/1983 | Japan | 568/835 |

Primary Examiner—Werren B. Lone
Attorney, Agent, or Firm—Sughrue, Mion, Zinn, Macpeak & Seas

[57] ABSTRACT

A process for producing cyclic olefins by catalytic hydration of cyclic olefins is disclosed, wherein the hydration is conducted in the presence of a crystalline aluminosilicate containing at least one member selected from the group consisting of titanium, zirconium, hafnium, chromium, molybdenum, tungsten, and thorium. The hydration reaction achieves high conversions and selectivities, and the catalytic activity is retained for a long time.

39 Claims, 1 Drawing Figure

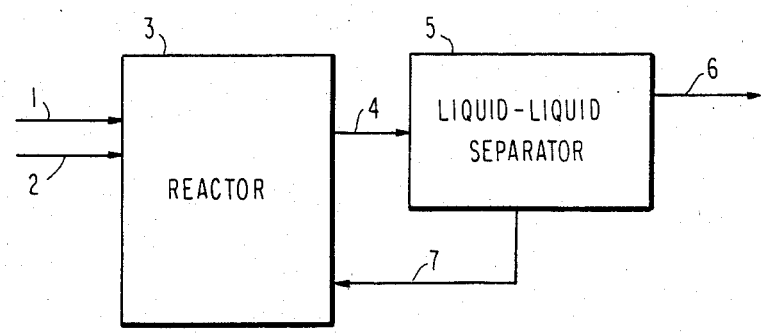

4,661,639

PROCESS FOR PRODUCING CYCLIC ALCOHOL

FIELD OF THE INVENTION

This invention relates to a novel process for producing a cyclic alcohol by catalytic hydration of a cyclic olefin.

BACKGROUND OF THE INVENTION

Conventionally known processes for producing cyclic alcohols by hydration of cyclic olefins include processes of indirect or direct hydration using highly concentrated mineral acids, particularly sulfuric acid. Other homogeneous catalysts that have been proposed for the reaction include aromatic sulfonic acids, as described in Japanese Patent Publication Nos. 8104/68 and 16123/68, heteropolyacids, such as phosphotungstic acid and phosphomolybdic acid, as described in Japanese Patent Application (OPI) No. 9746/78 (the term "OPI" as used herein refers to an "unexamined published application"), and the like.

However, when these homogeneous catalysts are used, the desired cyclic alcohol is present in the catalyst system and is difficult to separate and recover. Also, side reactions may occur to an extent which is more than negligible. Thus, separation and purification of the desired cyclic alcohol becomes difficult. In addition, regeneration of catalysts is impossible once they are deteriorated.

In order to overcome these defects, it has been proposed to use solid catalysts, for example, ion exchange resins are described in Japansese Patent Publication Nos. 15619/63 and 26656/69.

Such ion exchange resins, however, have the problem of reduction in size of the resin by mechanical disintegration, and problem of reduction in catalytic activity due to insufficient heat resistance of the resin. Thus such ion exchange resins are incapable of providing stable catalytic activity over a long period of time.

Also as a process of using a solid catalyst, it has been proposed to use crystalline aluminosilicates. Crystalline aluminosilicates are insoluble in water and have excellent mechanical strength and heat resistance, and thus would be expected to be utilizable as industrial catalysts. Thus, Japanese Patent Publication No. 45323/72 proposes a process for producing alcohols by hydration of olefins using dealkalized mordenite, clinoptilolite, or faujasite type zeolite as a catalyst.

Japanese Patent Publication No. 45323/72 describes in Example 4 an example of using cyclohexene as a cyclic olefin. According to Example 4, the reaction is conducted in an autoclave at a reaction temperature of from 200° to 210° C. for a reaction time of from 10 to 15 hours to obtain a conversion of water to cyclohexanol of as low as 0.05 to 0.06%. Calculation of the conversion of cyclohexene to cyclohexanol based on the above description gives a conversion of from 0.07 to 0.08%, and, in turn, calculation of the concentration of cyclohexanol in water based on this conversion gives a concentration of about 0.3%. No description appears therein as to selectivity of reacted cyclohexene to cyclohexanol and formation of by-products. To the contrary, with the hydration reaction of propylene or 1-butene also described in the same Example, although the reaction times are short, conversions of these straight chain olefins to corresponding alcohols are as high as 10 to 20% and 4 to 7%, respectively (calculated based on the conversions of water as in the above-described case, with the concentrations of the resulting alcohols in water, calculated based on these conversions, being 9 to 20% and 4 to 6%, respectively). Thus, the Example shows that hydration of cyclohexene to cyclohexanol is not practical due to too low a conversion to cyclohexanol as compared with the hydration of straight chain olefins.

U.S. Pat. No. 4,214,107 describes examples of gaseous phase catalytic hydration reaction of straight chain olefins, such as ethylene, propylene, etc., using HZSM-5 (proton-exchanged ZSM-5, made by Mobil Oil Corporation). However, no description are found therein with respect to cycloolefins.

U.S. Pat. No. 4,324,940 proposes a process of selectively reacting smaller olefins by effecting acid-catalyzed reactions of a mixed stream composed of smaller olefins and larger olefins having a crystalline zeolite. According to the description in this patent, the acid-catalyzed reactions include hydration reactions, and the olefins include cycloolefins. However, no examples thereof are given therein.

Japanese Patent Application (OPI) No. 70828/82 proposes a process for producing alcohols by hydration of olefins using specific crystalline aluminosilicates of Mobile Oil Corporation, such as ZSM-5 or ZSM-21. However, no examples of reacting cyclic olefins as olefins are given therein. Example 1 shows a reaction of propylene as a straight chain olefin, wherein the reaction is conducted at 200° C. for 2 hours followed by an after-treatment of removing unreacted propylene and the catalyst to obtain an aqueous filtrate containing 8.7 wt% isopropanol. On the other hand, Example 3 shows a reaction of 1-butene, wherein the reaction is conducted at 160° C. for 2 hours, followed by the same after-treatment as described above, to obtain an aqueous filtrate containing as low as 1.2 wt% sec-butyl alcohol.

Japanese Patent Application (OPI) No. 124723/83 proposes a process for producing alcohols by hydration of olefins using, as a catalyst, a partly dealuminated zeolite whose exchangeable ions have been wholly or partly exchanged with a hydrogen ion, or an ion of an element of the group II, VII or VIII of the Periodic Table, or of an earth metal element or rare earth element. However, reaction examples on cyclic olefins are not described therein. As examples of straight chain olefins, Example 1 shows a reaction of n-butylene, wherein the reaction is conducted at 170° C. for 2 hours, followed by removing unreacted n-butylene and the catalyst to obtain a filtrate containing at most 3.4 wt% sec-butyl alcohol.

Other processes proposed for hydration of olefins using crystalline aluminosilicates as catalysts include a process of using offretite as described in Japanese Patent Application (OPI) No. 70630/84, a process of using ferrierite as described in Japanese Patent Application (OPI) No. 70631/84, and a process of using erionite as described in Japanese Patent Application (OPI) No. 144723/84. However, none of these patent applications describes cyclic olefins as olefins to be reacted.

In view of the difference in reactivity between straight chain olefins and cyclic olefins shown in Japanese Patent Application (OPI) No. 4532/72 and the difference in reactivity among straight chain olefins shown in the Examples therein, extremely low reactivity is expected in the synthesis of cyclic alcohols from cyclic olefins using the catalysts specified by the aforesaid U.S. Pat. Nos. 4,214,107 and 4,324,940 and Japanese Patent Application (OPI) Nos. 70828/82, 124723/83, 124723/83, 70630/84, 70631/84 and 144723/84. In addition, side reactions that may occur in the above-described synthesis are unpredictable.

Thus, the above-described conventional processes, when applied to hydration of cyclic olefins, fail to achieve industrially sufficient catalytic activity, and require elevation of the reaction temperature for attaining an industrially satisfactory reaction rate. However, the hydration of cyclic olefins is an exothermic reaction, and the proportion of cyclic alcohols to cyclic olefins in the equilibrium composition decreases with increasing temperature. Therefore, a rise in the reaction temperature brings about reduction of concentrations of the desired cyclic alcohols, which necessitates a high cost for separation and recovery of cyclic alcohols. In addition, a rise of the reaction temperature leads to an increase of not only the hydration rate of cyclic olefins but also a conversion of cyclic alcohols to by-products due to isomerization and the like, resulting in reduction of selectivity to the desired reaction.

SUMMARY OF THE INVENTION

As a result of extensive investigations to solve the above-described problems, it has now been found that hydration of cyclic olefins can proceed with conspicuously heightened activity and selectivity lasting for a prolonged period of time, as compared with the conventional processes, by using, as a catalyst, a crystalline aluminosilicate containing at least one member selected from the group consisting of titanium, zirconium, hafnium, chromium, molybdenum, tungsten, and thorium.

That is, the present invention relates to a process for producing cyclic alcohols by catalytic hydration of cyclic olefins, which comprises using, as a catalyst, a crystalline aluminosilicate containing at least one member selected from the group consisting of titanium, zirconium, hafnium, chromium, molybdenum, tungsten, and thorium.

BRIEF DESCRIPTION OF THE DRAWING

The attached drawing illustrates an example of a flow sheet for practicing the present invention, wherein numeral 1 designates a feed pipe, 2 a feed pipe, 3 a reactor, 4 a discharge pipe, 5 a liquid-liquid separator, 6 a discharge pipe and 7 a recycle pipe.

DETAILED DESCRIPTION OF THE INVENTION

One of the features possessed by the present invention lies in that crystalline aluminosilicate containing at least one member selected from the group consisting of titanium, zirconium, hafnium, chromium, molybdenum, tungsten, and thorium shows high catalytic activity for the hydration of cyclic olefins, thus making it possible to obtain cyclic alcohols in a high yield as compared with conventional crystalline aluminosilicates that show only very low activity.

Another feature of the present invention is to suppress side reactions. For example, when cyclohexene is used as a cyclic olefin, possible side reactions include isomerization to methylcyclopentenes, e.g., 1-methycyclopentene, 3-methylcyclopentene, 4-methylcyclopentene, etc. These isomerized methylcyclopentenes are in turn converted to methylcyclopentanol, etc., upon hydration. Moreover, there are noted formation of high boiling substances by polymerization of cyclohexene to a dimer or oligomer, formation of diene compounds by dehydrogenation, and formation of high boiling substances resulting from further conversion of these by-products. By-production of ethers or the like derived from the desired cyclohexanol also takes place.

Most of these side reactions are ascribed to lability of cyclic olefins which are scarcely or never observed in the case of reactions of straight chain olefins. By the use of the specific catalyst according to the present invention, such side reactions are strikingly suppressed. This suppression effect significantly inhibits reduction of catalytic activity with time, and, as a result, makes it possible to maintain high activity and high selectivity for an extended period of time.

The crystalline aluminosilicate containing at least one member selected from the group consisting of titanium, zirconium, hafnium, chromium, molybdenum, tungsten, and thorium (hereinafter simply referred to as "metal-containing crystalline aluminosilicate") which can be used in the present invention is a crystalline aluminosilicate in which at least one member selected from the group consisting of titanium, zirconium, hafnium, chromium, molybdenum, tungsten, and thorium (hereinafter referred to as "titanium (Ti), etc.") is physically or chemically bonded to the crystalline aluminosilicate through ionic bonding, covalent bonding or coordinate bonding, and include those wherein two or more of titanium, etc., are bonded to one active site of a crystalline aluminosilicate.

The mechanism accounting for the high activity exerted by such a crystalline aluminosilicate containing titanium, etc., has not yet been clarified, but it is assumed that new active sites for hydration are formed on the crystalline aluminosilicate in such a manner that titanium, etc., is included in the active sites. Further, when water and organic materials are copresent in the reaction system, as in the case of the present invention, a crystalline aluminosilicate, in general, preferentially adsorbs water or the cyclic alcohols produced, thereby suppressing adsorption of the second component, i.e., cyclic olefins. At the same time, dehydration of the cyclic alcohols, which is the reverse of hydration, proceeds, resulting in reduction of the rate of hydration. On the other hand, the heat of adsorption of cyclic olefins onto titanium, etc., that form the active sites in the present invention is considerably higher compared with the heat of adsorption of cyclic olefins onto other elements. Accordingly, in the catalyst of the present invention, the active site in which titanium, etc., take part are assumed to accelerate selective adsorption of cyclic olefins on the catalyst, and thereby greatly improve efficiency of the hydration. Therefore, the catalyst employed in the present invention exhibits high activity even under a condition wherein liquid phase water is present in the reaction system.

When a powder-type catalyst is used in the present invention, dispersibility of the catalyst in water can be improved. This appears to be ascribable to enhanced compatibility with water as well as to the above-mentioned enhanced capability of adsorbing cyclic olefins.

In the case wherein cyclic olefins having large molecular sizes are used as reactants, the rate of diffusion of such olefins in micropores of the crystalline aluminosilicate used as a catalyst is low due to their large molecule size, in marked contrast to straight chain olefins. As a result, it appears that acid sites inside the catalyst do not substantially participate in the reaction. This may also be surmised from the fact that reaction rates of the hydration reaction of cyclic olefins conducted in the presence of the conventional crystalline aluminosilicates are much slower than those of straight chain olefins.

As a result of measurement of external surface acid sites (acid sites outside micropores) and total acid sites according to a pulse adsorption method, described hereinafter, it has been found that, as compared with the crystalline aluminosilicate catalyst containing no metal such as titanium, the metal-containing catalyst according to the present invention has a remarkably increased number of external surface acid sites, while the total acid sites of these aluminosilicates being substantially equal. In other words, the latter has a larger population ratio of external surface acid sites to total acid sites than the former. The effect of the present invention can be explained by this larger population of external surface acid sites as well as by the fact that the hydration of cyclic olefins proceeds at the external surface of the catalyst. On the other hand, when straight chain olefins having a small molecular size were subjected to hydration in the presence of the metal-containing catalyst according to the present invention, the results obtained were substantially equal to those obtained using the catalyst containing no metal. Besides, a process using straight chain olefins as reactants, e.g., Japanese Patent Application (OPI) No. 70630/84 suggests from page 163, column 4, line 7 up to page 164, column 1, line 4 that the catalyst which can be used may contain a monovalent alkali metal ion or a polyvalent metal ion. However, neither working example thereof nor the effects brought about by the use of such a catalyst is described therein. Hence, the effect of the present invention using cyclic olefins as reactants can not be expected from the prior art.

As a result of further investigations, it has also been found that the activity of the metal-containing crystalline aluminosilicate in hydration of cyclic olefins can be enhanced in the presence of an acid in an aqueous solution thereof.

The above fact is a surprising finding that has never been predicted. That is, the acid in the form of its aqueous solution seems to achieve a synergestic effect at a concentration that does not per se produce any hydration activity. This synergestic effect cannot be fully accounted for by a mere sum of the effects produced by each of the metal-containing crystalline aluminosilicate and the acid in an aqueous solution thereof. The reasons for the heightened activity of the metal-containing crystalline aluminosilicate in the presence of an acid in an aqueous solution thereof are not clear, but may possibly be as follows. Firstly, protons of an acid in the aqueous solution thereof are supposed to be coordinated to the non-covalent electron-pair of oxygen atoms on the surface of the metal-containing crystalline aluminosilicate. An electron attractive effect by this coordination may increase acid strength of the catalyst. Secondly, in the case of using an inorganic compound which acts as a Lewis acid, the above-described effect can be manifested even with a low acidity in an aqueous solution. From this fact, it is assumed that direct mutual interaction between the hydration active sites of the metal-containing crystalline aluminosilicate and the Lewis acid molecules induces formation of new hydration active sites having high activity to thereby heighten affinity for olefins and to greatly increase the hydration activity.

The catalysts that can be used in the present invention can be obtained by incorporating a metal, such as titanium, etc., in known crystalline aluminosilicates by treating with sources for such a metal. The crystalline aluminosilicates that can be used as catalyst precursors include mordenite, faujasite, clinoptilolite, chabazite, erionite, ferrierite, L type zeolite, ZSM type zeolite (made by Mobil Oil Corporation) and other pentasil type zeolite.

Among them, pentasil type zeolite is effective. In particular, pentasil type zeolite prepared by using a lower alkylurea or a lower alkylthiourea as a template, as described in Japanese Patent Application No. 188165/84, produces good results ensuring the effect of the present invention.

The lower alkylurea is represented by the formula:

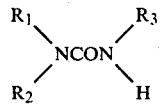

wherein one or two of $R_1$, $R_2$ and $R_3$ each represents an alkyl group having from 1 to 3 carbon atoms, with the rest being a hydrogen atom. Preferred examples of the lower alkylurea include methylurea, 1,3-dimethylurea, 1,1-dimethylurea, ethylurea, 1,1-diethylurea, 1,3-diethylurea, n-propylurea, isopropylurea, 1-methyl-1-ethylurea, 1-methyl-3-ethylurea, etc.

The lower alkylthiourea is represented by the formula:

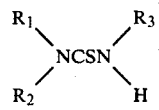

wherein $R_1$, $R_2$ and $R_3$ are as defined above. Preferred examples of the lower alkylthiourea include methylthiourea, 1,3-dimethylthiourea, 1,1-dimethylthiourea, ethylthiourea, 1,1-diethylthiourea, 1,3-diethylthiourea, n-propylthiourea, isopropylthiourea, 1-methyl-1-ethylthiourea, 1-methyl-3-ethylthiourea, etc.

Incorporation of a metal in these catalyst precursors can be effected by any known methods, such as a method in which the crystalline aluminosilicate is immersed in an aqueous solution of a compound of titanium, zirconium, hafnium, chromium, molybdenum, tungsten, or thorium at room temperature or under heating to thereby exchange and/or adsorb titanium, etc., a method in which a mixture of an aqueous solution or slurry of the above-described compound of titanium, etc., and a crystalline aluminosilicate is evaporated to dryness, a method comprising contacting the above-described compound of titanium, etc., with a crystalline aluminosilicate in an organic solvent, and the like.

Examples of the compounds of titanium, etc., which can be used in the present invention include titanium halides, titanium nitrate, titanium sulfate, and titanates as titanium sources; zirconium halides, zirconium nitrate, and zirconium sulfate as zirconium sources; hafnium halides, hafnium nitrate and hafnium sulfate as hafnium sources; chromium (II) chloride, chromium (II) sulfate, and chromium (III) nitrate as chromium sources; molybdenum (VI) oxide and ammonium molybdate as molybdenum sources, tungsten (V) chloride as tungsten sources; and thorium nitrate, thorium chloride, and thorium sulfate as thorium sources.

The aqueous solution or aqueous slurry of these metal compounds which can be used for treating the crystalline aluminosilicate preferably has a concentration of from about 0.001 to 20% by weight, and more preferably from 0.01 to 10% by weight. The same conditions are preferably applied to the treatment using an organic solvent. The treatment according to the immersion method is carried out at from room temperature to 100° C., and preferably from room temperature to 80° C., under atmospheric pressure. The treatment according to the evaporation to dryness method is carried out at from 40° C. to 100° C., and preferably from 60° to 100° C., at atmospheric pressure. The treatment may also be effectively conducted at high temperatures under pressure. In the case of effecting the treatment in water, the metal compound may be converted to substantially different compounds due to reactions, such as hydrolysis. Further, the product obtained by these treatments may be subjected to after-treatment, such as ion-exchange, washing with water, drying, calcination, reduction, and the like.

In the catalysts which can be used in the present invention, the chemical species or existing state of the metal, such as titanium, etc., present therein is not particularly limited, but it is preferred that titanium, etc. be present in the form of its cation, hydroxide, oxide or metal.

The amount of the metal to be incorporated in the crystalline aluminosilicate preferably ranges from about 0.002 to 5.0 mol/Kg (i.e., mole per kilogram), more preferably from 0.004 to 2.0 mol/Kg, and most preferably from 0.01 to 1.0 mol/Kg, in terms of mole number of an element per unit weight of the catalyst.

The crystalline aluminosilicate, after being treated with the metal compound, may contain a proton or other cations. It is also effective that all the active sites which participate in hydration become active sites in which titanium, etc. take part in.

The molar ratio of silica to alumina in the crystalline aluminosilicate which can be used as a catalyst precursor is not particularly restricted, but is preferably 10/1 or more, and more preferably 20/1 or more. If the molar ratio of silica to alumina is high, the acid strength of acid sites that are active sites of the hydration reaction increases, and, in contrast, the amount of the acid sites is remarkably reduced. Therefore, the usual upper limit of the silica to alumina molar ratio is about 300/1, and preferably is 100/1.

The population ratio of external surface acid sites to total acid sites in the crystalline aluminosilicate used in the present invention is not particularly restricted. However, cyclic olefins that are used in the present invention have a relatively larger molecule size than straight chain olefins. As a result, the rate of diffusion of the cyclic olefin into the inside of the crystalline aluminosilicate particles is expected to be smaller irrespective of whether the reaction is performed in a gaseous or liquid phase. The influence of the large molecule size of cyclic olefins is particularly pronounced in a liquid phase. In other words, the activity of the catalyst according to the present invention is believed to depend predominantly on the population of external surface acid sites (acid sites outside micropores). Accordingly, it is effective to use a crystalline aluminosilicate having a relatively larger population ratio of external surface acid sites to total acid sites in number, preferably of not less than 0.02, more preferably of not less than 0.05, and most preferably of not less than 0.2.

The incorporation of titanium, etc. in a crystalline aluminosilicate serves to increase acid sites on the external surface of the aluminosilicate to thereby conspicuously increase active sites in number. This effect can be exhibited in treating not only crystalline aluminosilicates having small ratios of external surface acid sites but also those having larger ratios of external surface acid sites. The catalysts prepared by treating crystalline aluminosilicates having large populations of external surface acid sites with titanium, etc., have great significance in industrial production of cyclic alcohols.

The kind of cation species exchangeable in the crystalline aluminosilicate which can be used in the present invention is not particularly limited. However, it is most effective to use the catalyst after proton exchange.

In the present invention, the catalyst may have any form, such as a powder, graules, molded articles having specific shapes, and the like. In the case of using molded articles, alumina, silica, titania, etc., may be used as a carrier.

The acids which can be used in the present invention are substances which exhibit acidity when mixed with water. The acids may be modified during reaction due to hydrolysis, pyrolysis, etc., as long as they show acidity in an aqueous solution thereof. The acids which can be used include inorganic compounds which act as Bronsted acids, such as sulfuric acid, nitric acid, hydrochloric acid, molybdic acid, tungstic acid, heteropoly acid, etc.; inorganic compounds which act as Lewis acids, such as halides of aluminum family elements, transition metal halides, transition metal sulfates, transition metal complexes, etc.; carboxylic acids, such as formic acid, acetic acid, propionic acid, trifluoroacetic acid, etc.; and organic sulfonic acids, such as trifluoromethanesulfonic acid, methanesulfonic acid, benzenesulfonic acid, p-toluenesulfonic acid, etc. The term "Bronsted acid" as used herein means a protic acid, i.e., a proton-donating acid, and the term "Lewis acid" as used herein means an aprotic acid. These acids can be used alone or as a mixture of two or more thereof.

The acid is present in the reaction system in an aqueous solution thereof. If the acid concentration is too high, separation and recovery of the reaction product becomes very difficult. If the acid concentration is too low, the acid strength as an aqueous solution is insufficient. Accordingly, the acid concentration employed in the present invention is preferably in the range of from 0.001 to 5 mol/l, more preferably from 0.005 to 2 mol/l, and most preferably from 0.01 to 1 mol/l, though varying depending on the type of the acid. When the acid in the form of an aqueous solution thereof at the above specified concentration is used alone as a catalyst without using the metal-containing crystalline aluminosilicate, hydration activity is scarcely exhibited.

In the cases when dicarboxylic acids, such as succinic acid, glutaric acid, adipic acid, etc., are used as acids, they are preferably used at a concentration of from 0.5 to 5 mol/l, and more preferably from 1 to 5 mol/l.

The cyclic olefins which can be used in the present invention preferably include cyclic olefins having from 5 to 12 carbon atoms. Specific examples thereof are cyclopentene, methylcyclopentenes, cyclohexene, methylcyclohexenes, cyclooctene, cyclododecene, and the like.

The reaction is carried out in a commonly employed manner, such as a fluidized bed system, a batch system with stirring, a continuous system, and the like. Low reaction temperature are advantageous in view of equilibrium of the hydration of cyclic olefins and suppression of side reactions. On the other hand, high reaction temperatures are advantageous from the standpoint of reaction rate. In the present invention, the reaction temperature usually ranges from 50° to 250° C., preferably from 60° to 200° C., and more preferably from 70° to 160° C., though depending on the type of the cyclic olefins used. The reaction pressure is not particularly restricted, and the cyclic olefin and water may be present in either a gaseous phase or a liquid phase. In particular, when water is present in a liquid phase, it is generally the case that the catalyst is surrounded by water in the neighborhood of its active sites, causing reduction of the reaction rate. The reaction in accordance with the present invention particularly shows its effectiveness in such a case. A molar ratio of the cyclic olefin to water can be selected from a broad range and also varies depending on whether the reaction is carried out continuously or batchwise. Nevertheless, too high a proportion of the cyclic olefin or water to other reactants is not practical because the reaction rate decreases. Accordingly, the molar ratio of the cyclic olefin to water, when reacted, e.g., in a batch system, preferably falls within the range of from 0.01 to 100, and more preferably from 0.03 to 10.

The weight ratio of the cyclic olefin to the catalyst, when reacted in a batch system, preferably ranges from 0.005 to 100, and more preferably from 0.05 to 10. The reaction time is preferably from 3 to 300 minutes, and more preferably from 10 to 180 minutes.

The reaction system may contain, in addition to the cyclic olefin and water, an inert gas, e.g., nitrogen, hydrogen, helium, argon, carbon dioxide, etc., an aliphatic saturated hydrocarbon, an aromatic hydrocarbon, an oxygen-containing organic compound, a sulfur-containing organic compound, a halogen-containing organic compound, and the like.

Thus, according to the present invention, a cyclic alcohol can be produced from a cyclic olefin by catalytic hydration with high conversion and selectivity as compared with conventional processes by using a crystalline aluminosilicate containing at least one member selected from titanium, zirconium, hafnium, chromium, molybdenum, tungsten, and thorium as a catalyst, and the reactivity can be retained for a prolonged period of time.

The present invention is now illustrated in greater detail by referring to the following Examples and Comparative Examples, but the present invention is not limited thereto. In these examples, the population of external surface acid sites (acid sites outside micropores) and total acid sites were measured according to the following pulse adsorption method.

MEASUREMENT OF ACID SITES

A gas chromatography, GC-7A, and a data-processing apparatus, CR-1A (both made by Shimadzu Seisakusho Ltd.), were used as measuring equipment. A sample (0.2 g to 1 g) was loaded in a stainless steel-made column of 4 mm in inside diameter and 80 mm in overall length, and the column was mounted to a sample-side flow path placed in a thermostatic chamber of the gas chromatograph. Helium gas was introduced into the column as a carrier gas at a flow rate of 50 ml/min. and, at the same time, the temperature within the chamber was increased to 325° C. by heating. Two hours after heating, adsorption procedure was initiated. Portions of a definite amount (0.2 to 2 $\mu$l) of an amine (pyridine, 4-methylquinoline, or tributylamine) were intermittently injected at definite intervals (2 minutes to 5 minutes) through an injection opening on the sample-size flow path using a microsyringe. At the other end, the carrier gas having traveled through the column was analyzed using a FID (flame ionization detector) to obtain a chromatogram showing periodical peaks of amine. With the increase in the number of the injection, the amount of adsorbed amine approaches near to a saturation level, and the amount of non-adsorbed amine increases. Thus, in the above-mentioned chromatogram, peak area $S_i$ corresponding to non-adsorbed amine in the i-th injection of amine (e.g., peak area $S_5$ corresponding to the non-adsorbed amine in the 5th injection of amine) gradually approaches the area $S_0$ which corresponds to the amount of injected amine, $d_0$ $\mu$mol. Therefore, the amount of adsorbed amine per unit weight of sample, $A_0$ ($\mu$mol/g), can be given by $$A_0 = \frac{1}{W} \sum_{i=1}^{\infty} \left(1 - \frac{S_i}{S_0}\right) d_0$$

wherein W (in grams) represents the weight of a sample.

In the present invention, injection was repeated n times at which $S/S_0 \geq 0.98$, and the amount of adsorbed amine, A ($\mu$mol/g), was calculated according to the following formula:

$$A = \frac{1}{W} \sum_{i=1}^{\infty} \left(1 - \frac{S_i}{S_0}\right) d_0$$

The population ratio of external surface acid sites to total acid sites of a particular crystalline aluminosilicate was determined as follows. That is, in micropores of the crystalline aluminosilicate, when the maximum micropore diameter is represented by $a_{max}$ and the minimum micropore diameter is represented by $a_{min}$, an amount of adsorbed amine corresponding to external surface acid sites, $A_{out}$, is determined using amine I having a kinetic diameter of $a_1 > a_{max}$, and an amount of adsorbed amine corresponding to total acid sites, $A_{total}$, is determined using amine II having a kinetic diameter of $a_2 < a_{min}$ (concerning "kinetic diameter", see D. W. Breck, Zeolite Molecular Sieves, Wiley-Interscience, 1974, pp 634–635). The population ratio of external surface acid sites to total acid sites, R, can be calculated by the following formula:

$$R = A_{out}/A_{total}$$

From measuring the population ratio, R, a combination of pyridine and tributylamine was used in Examples 8 and 9 and Comparative Example 2, and a combination of pyridine and 4-methylquinoline was used in the other Examples and Comparative Examples.

EXAMPLE 1

I. Preparation of Catalyst (1) A mixture of 32.2 g of aluminum sulfate, 328 g of sodium chloride, 92.6 g of concentrated sulfuric acid, 139 g of tetrapropylammonium bromide and 1896 g of water was added to a mixture of 1112 g of Q-brand sodium silicate (28.9 wt% SiO$_2$, 8.9 wt% Na$_2$O) and 1386 g of water. The resulting mixture was mixed intimately in a high speed stirring homogenizer and then maintained at 150° C. for 4 days in an autoclave while stirring. The cooled reaction product was filtered, washed with water, dried at 120° C. for 8 hours and then calcined at 550° C. for 5 hours in an air stream. The resulting solid product was crystals and was identified as ZSM-5 by X-ray diffractiometry (Precursor A). The above-described procedures were repeated 3 times to obtain additional amounts of Precursor A.

400 g of Precursor A was added to 4 liters of a 2M aqueous solution of ammonium chloride, and the mixture was maintained at 80° C. for 2 hours while stirring. After filtration, the same procedure was repeated twice to effect ion exchange. The product was washed with water, filtered, dried, and calcined at 400° C. for 2 hours to obtain proton-exchanged type ZSM-5 (Precursor B). The above-described procedures were repeated 3 times to obtain additional amount of Precursor B.

(2) To a mixture of 0.38 g of titanium tetrachloride and 100 ml of water was added 10 g of Precursor A, and the mixture was stirred at room temperature for 10 hours. The thus treated mixture was washed with water and filtered. The solid product was dried and calcined at 400° C. for 2 hours in an air stream to produce Catalyst 1.

(3) To a mixture of 19 g of titanium tetrachloride and 5 liters of water was added 500 g of Precursor B, and the mixture was stirred at room temperature for 8 hours. The thus treated mixture was washed with water and filtered. The solid product was dried at 80° C. in a nitrogen atmosphere to produce Catalyst 2.

(4) Catalyst 2 was calcined at 400° C. for 2 hours in an air stream to produce Catalyst 3.

(5) Catalyst 3 was heated at 400° C. for 2 hours in a hydrogen stream to produce Catalyst 4.

The titanium content and the $SiO_2/Al_2O_3$ molar ratio as measured by X-ray fluorometry, and the ratio of external surface acid sites to total acid sites as measured by the pulse adsorption method in each of the catalysts obtained above are shown in Table 1.

II. Hydration

Ten grams of each of the catalysts as above prepared, the resulting mixture was stirred at room temperature for 8 hours. The thus treated mixture was washed with water, filtered, dried, and calcined at 400° C. for 2 hours in an air stream to produce Catalyst 5.

The hydration reaction was carried out in the same manner as described in Example 1 except for using the above-described Catalyst 5. The physical properties and results of hydration are shown in Table 1.

EXAMPLE 3

To a mixture of 11.6 g of α-titanic acid and 200 ml of water was added 100 g of Precursor B. The resulting mixture was heated on a water bath and then evaporated to dryness. After drying at 130° C. for 8 hours, the solid product was calcined at 400° C. in an air stream to produce Catalyst 6.

Hydration reaction was carried out in the same manner as described in Example 1 except for using the above obtained Catalyst 6. The physical properties of the catalyst and the result of the hydration are shown in Table 1.

EXAMPLE 4

To a mixture of 0.76 g of titanium tetrachloride and 200 ml of water was added 20 g of Catalyst 3, and the mixture was stirred at room temperature for 8 hours. The thus treated mixture was washed with water and filtered. The solid product was dried and calcined at 400° C. for 2 hours in an air stream. The resulting product was additionally subjected to the above-described treatment with titanium four times to produce Catalyst 7.

Hydration reaction was carried out in the same manner as in Example 1 except for using Catalyst 7 as prepared above. The physical properties of the catalyst and the results of the hydration are shown in Table 1.

COMPARATIVE EXAMPLE 1

Hydration reaction was carried out in the same manner as in Example 1 except for using Precursor B as a catalyst. The physical properties of the catalyst and the results of the hydration are shown in Table 1.

TABLE 1

| Example No. | Catalyst | Element Contained and Content (mol/kg) | | Silica/Alumina Molar Ratio in the Catalyst | Ratio of External Surface Acid Sites/ Total Acid Sites of the Catalyst | Cyclohexanol Concentration (wt %) in Oil Phase after Hydration Reaction |
|---|---|---|---|---|---|---|
| 1 | 1 | Ti | 0.14 | 57 | 0.07 | 10.8 |
| 1 | 2 | Ti | 0.12 | 58 | 0.07 | 12.3 |
| 1 | 3 | Ti | 0.12 | 58 | 0.08 | 13.0 |
| 1 | 4 | Ti | 0.12 | 59 | 0.07 | 11.1 |
| 2 | 5 | Ti | 0.04 | 57 | 0.06 | 11.3 |
| 3 | 6 | Ti | 0.93 | 57 | 0.08 | 13.6 |
| 4 | 7 | Ti | 0.42 | 60 | 0.08 | 13.5 |
| Comparative Example 1 | Precursor B | — | — | 57 | 0.05 | 3.8 |

30 g of water and 15 g of cyclohexene were placed in a 100 ml-volume stirring autoclave, and the mixture was reacted at 120° C. for 15 minutes while stirring. After the reaction, the product was analyzed by gas chromatography, and the results obtained are shown in Table 1. The product was found to solely comprise cyclohexanol, with no other product being detected.

EXAMPLE 2

To a mixture of 0.76 g of titanium tetrachloride and 1.0 liter of water was added 100 g of Precursor B, and

EXAMPLE 5

(1) Precursor A and Precursor B prepared in Example 1 were used as catalyst precursors.

(2) Ten grams of Precursor A was added to a mixture of 0.51 g of chromium (II) chloride hexahydrate and 100 ml of water, and the resulting mixture was stirred at room temperature for 8 hours. The resulting mixture was washed with water and filtered. The solid product was dried and calcined at 400° C. for 2 hours under an air stream to obtain Catalyst 8.

(3) To a mixture of 12.6 g of chromium (II) chloride hexahydrate and 2.5 liters of water was added 250 g of Precursor B, and the resulting mixture was stirred at room temperature for 8 hours. The resulting mixture was washed with water and filtered. The solid product was dried at 80° C. in a nitrogen atmosphere to obtain Catalyst 9.

(4) Catalyst 9 obtained above was calcined at 400° C. for 2 hours in an air stream to obtain Catalyst 10.

(5) Catalyst 10 obtained above was heated at 400° C. for 3 hours to obtain Catalyst 11.

The chromium content and $SiO_2/Al_2O_3$ molar ratio as determined by X-ray fluorometric analysis, and the ratio of external surface acid sites to total acid sites as determined by the pulse adsorption method for each of catalysts obtained above are shown in Table 2 below.

Further, the hydration reaction was carried out under the same conditions as described in Example 1, except using catalysts obtained as described above and a reaction temperature of 122° C. The results obtained are also shown in Table 2. The product obtained was found to comprise solely cyclohexanol, and no other products were detected.

(4) Catalyst 13 was calcined at 400° C. for 2 hours in an air stream to obtain Catalyst 14.

(5) Catalyst 14 was heated at 400° C. for 3 hours in a hydrogen stream to obtain Catalyst 15.

(6) To a mixture of 13.5 g of thorium (IV) nitrate and 100 ml of water was added 50 g of Precursor B. The resulting mixture was evaporated to dryness on a water bath at 100° C. The solid product was dried at 130° C. for 12 hours, and then calcined at 400° C. for 4 hours in an air stream to obtain Catalyst 16.

The thorium content and $SiO_2/Al_2O_3$ molar ratio as measured by X-ray fluorometric analysis and the ratio of external surface acid sites to total acid sites as measured by the pulse adsorption method for each of the above-prepared catalysts are shown in Table 3.

Hydration reaction was carried out under the same conditions as used in Example 1, except that each of the catalysts as above obtained was used, at a reaction temperature was 118° C. and a reaction time was 14 minutes. The results obtained are also shown in Table 3. The product was found to comprise solely cyclohexanol, with no other products being detected.

EXAMPLE 7

To a mixture of 1.4 g of thorium (IV) nitrate and 200

TABLE 2

| Example No. | Catalyst | Element Contained and Content (mol/kg) | | Silica/Alumina Molar Ratio in the Catalyst | Ratio of External Surface Acid Sites/ Total Acid Sites of the Catalyst | Cyclohexanol Concentration (wt %) in Oil Phase after Hydration Reaction |
|---|---|---|---|---|---|---|
| 5 | 8 | Cr | 0.15 | 58 | 0.06 | 9.3 |
| 5 | 9 | Cr | 0.13 | 58 | 0.07 | 11.3 |
| 5 | 10 | Cr | 0.13 | 60 | 0.08 | 12.0 |
| 5 | 11 | Cr | 0.13 | 59 | 0.07 | 10.9 |

EXAMPLE 6

(1) Precursor A and Precursor B as prepared in Example 1 were used as catalyst precursors.

(2) Ten grams of Precursor A was added to a mixture of 0.72 g of thorium (IV) nitrate and 100 ml of water, and the mixture was stirred at room temperature for 8 hours. The resulting mixture was washed with water and filtered. The solid product was dried and calcined at 400° C. for 2 hours in an air stream to obtain Catalyst 12.

(3) To a mixture of 18 g of thorium (IV) nitrate and 2.5 liters of water was added 250 g of Precursor B, and the mixture was stirred at room temperature for 12 hours. The resulting mixture was washed with water and filtered. The solid material was dried at 80° C. in a nitrogen atmosphere to obtain Catalyst 13.

ml of water was added 20 g of Catalyst 14, followed by stirring at room temperature for 10 hours. The resulting mixture was washed with water and filtered, and the solid was dried and calcined at 400° C. for 2 hours in an air stream. The resulting solid was then further subjected 3 times to the above treatment for incorporating thorium to obtain Catalyst 17.

Hydration reaction was carried out under the same conditions as used in Example 6, except using Catalyst 17 as prepared above. The properties of the catalyst and results of the hydration reaction are shown in Table 3 below.

TABLE 3

| Example No. | Catalyst | Element Contained and Content (mol/kg) | | Silica/Alumina Molar Ratio in the Catalyst | Ratio of External Surface Acid Sites/ Total Acid Sites of the Catalyst | Cyclohexanol Concentration (wt %) in Oil Phase after Hydration Reaction |
|---|---|---|---|---|---|---|
| 6 | 12 | Th | 0.10 | 57 | 0.06 | 8.6 |
| 6 | 13 | Th | 0.09 | 58 | 0.07 | 11.2 |
| 6 | 14 | Th | 0.09 | 58 | 0.07 | 11.5 |
| 6 | 15 | Th | 0.09 | 59 | 0.07 | 10.8 |
| 6 | 16 | Th | 0.51 | 59 | 0.08 | 12.5 |
| 7 | 17 | Th | 0.41 | 59 | 0.08 | 13.0 |

EXAMPLE 8

Synthetic mordenite (TSZ 644 manufactured by Toyo Soda Manufacturing Co., Ltd.) was ion-exchanged with a 2M ammonium chloride aqueous solution and then calcined to obtain proton-exchanged type mordenite (Precursor C).

To a mixture of 3.78 g of titanium tetrachloride and 1.0 liter of water was added 100 g of the above Precursor C, and the resulting mixture was kept at 80° C. for 2 hours while stirring. The mixture thus treated was washed with water, filtered, dried and calcined at 400° C. for 2 hours in an air stream to obtain Catalyst 18.

Hydration reaction was carried out under the same conditions as used in Example 1, except using Catalyst 18 as obtained above and a reaction time of 80 minutes. Properties of the catalyst and the results of the hydration reaction are shown in Table 4.

COMPARATIVE EXAMPLE 2

Hydration reaction was carried out under the same conditions as used in Example 8, except using Precursor C as a catalyst. Properties of the catalyst and results of the hydration reaction are shown in Table 4 below.

EXAMPLE 9

To a mixture of 3.3 g of thorium (IV) nitrate and 200 ml of water was added 20 g of Precursor C as described above, and the resulting mixture was kept at 80° C. for 2 hours while stirring. The mixture thus treated was washed with water, filtered, dried and calcined at 400° C. for 2 hours in an air stream to obtain Catalyst 19.

Hydration reaction was carried out under the same conditions as used in Example 1 but using Catalyst 19, a reaction temperature of 118° C. and a reaction time of 65 minutes.

Properties of the catalyst and results of the hydration reaction are also shown in Table 4 below.

The hydration reaction was carried out under the same conditions as used in Example 1, except using Catalyst 20 as obtained above. Properties of the catalyst and the results of the hydration reaction are shown in Table 5 below.

EXAMPLE 11

A catalyst was prepared in the same manner as described in the catalyst preparation of Example 10, except using 3.70 g of hafnium sulfate instead of the zirconium nitrate, to obtain Catalyst 21.

Hydration reaction was carried out under the same conditions as used in Example 1, except using Catalyst 21 as obtained above. Properties of the catalyst and the results of the hydration reaction are also shown in Table 5.

EXAMPLE 12

To a mixture of 0.82 g of molybdenum (V) chloride and 200 ml of water was added 20 g of Precursor B, and the resulting mixture was stirred at room temperature for 12 hours. The mixture thus treated was washed with water, filtered, dried, and calcined at 400° C. for 4 hours in an air stream to obtain Catalyst 22.

Hydration reaction was carried out under the same conditions as used in Example 10, except for using a reaction temperature of 122° C. Properties of the catalyst and results of the hydration reaction are also shown in Table 5.

EXAMPLE 13

To a mixture of 1.0 g of tungstic acid and 100 ml of water was added 20 g of Precursor B, and the resulting

TABLE 4

| Example No. | Catalyst | Element Contained and Content (mol/kg) | | Silica/Alumina Molar Ratio in the Catalyst | Ratio of External Surface Acid Sites/ Total Acid Sites of the Catalyst | Cyclohexanol Concentration (wt %) in Oil Phase after Hydration Reaction | By-Products* Formed in Hydration Reaction (wt %) | | |
|---|---|---|---|---|---|---|---|---|---|
| | | | | | | | A | B | C |
| 8 | 18 | Ti | 0.14 | 21 | 0.04 | 8.0 | 0.10 | 0.05 | 0.03 |
| 9 | 19 | Th | 0.23 | 21 | 0.03 | 7.1 | 0.06 | 0.05 | 0.05 |
| Comparative Example 2 | Precursor C | — | — | 20 | 0.02 | 4.0 | 0.8 | 0.44 | 0.14 |

Note:
*By-Products:
A: Methylcyclopentene
B: Dicyclohexyl ether
C: Cyclohexene dimer

EXAMPLE 10

To a mixture of 4.29 g of zirconium nitrate tetrahydrate and 500 ml of water was added 50 g of Precursor B, and the resulting mixture was stirred at room temperature for 8 hours. The mixture thus treated was washed with water, filtered, dried and calcined at 400° C. for 2 hours in an air stream to obtain Catalyst 20.

mixture was evaporated to dryness on a water bath at 90° C. After drying at 130° C. for 20 hours, the residue was calcined at 400° C. for 8 hours in an air stream to obtain Catalyst 23.

Hydration reaction was carried out under the same conditions as used in Example 12, except using Catalyst 23 as obtained above. Properties of the catalyst and results of the hydration reaction are also shown in Table 5 below.

TABLE 5

| Example No. | Catalyst | Element Contained and Content (mol/kg) | | Silica/Alumina Molar Ratio in the Catalyst | Ratio of External Surface Acid Sites/ Total Acid Sites of the Catalyst | Cyclohexanol Concentration (wt %) in Oil Phase after Hydration Reaction |
|---|---|---|---|---|---|---|
| 10 | 20 | Zr | 0.18 | 58 | 0.07 | 10.9 |
| 11 | 21 | Hf | 0.16 | 58 | 0.08 | 8.6 |
| 12 | 22 | Mo | 0.10 | 60 | 0.06 | 9.1 |

TABLE 5-continued

| Example No. | Catalyst | Element Contained and Content (mol/kg) | Silica/Alumina Molar Ratio in the Catalyst | Ratio of External Surface Acid Sites/ Total Acid Sites of the Catalyst | Cyclohexanol Concentration (wt %) in Oil Phase after Hydration Reaction |
|---|---|---|---|---|---|
| 13 | 23 | W 0.18 | 59 | 0.06 | 8.0 |

EXAMPLE 14

In a 1 liter-volume autoclave, 100 g of Catalyst 3, 300 g of water, and 150 g of cyclohexene were charged, and the mixture was reacted at 100° C. for 5 hours while stirring. The cyclohexanol concentration in the oil phase was 21.8%. The oil phase was separated from the reaction mixture by decantation. To the catalyst-containing aqueous slurry remaining in the reactor was added additional 150 g of cyclohexene, and the reaction was effected under the same conditions as described above. The above-described procedures were repeated 40 times in total. The finally obtained oil phase was found to contain cyclohexanol at a concentration of 22.1 wt%, and substantially no reduction of catalytic activity and selectivity was observed. Further, the catalyst had a white color, indicating no change, such as would be indicated by coloration.

COMPARATIVE EXAMPLE 3

Hydration reaction was repeatedly conducted under the same conditions as in Example 14, except using Precursor B as a catalyst. The cyclohexanol concentration in the oil phase obtained by the first reaction was 5.4 wt%, whereas that in the oil phase of the final reaction mixture was 2.6 wt%. Furthermore, the catalyst turned to a dark brown color.

EXAMPLE 15

A mixture of 22.5 g of aluminum sulfate, 230 g of sodium chloride, 65.0 g of concentrated sulfuric acid, 97 g of tetrapropylammonium bromide and 1330 g of water was added to a mixture of 780 g of Q-brand sodium silicate and 970 g of water. The resulting mixture was intimately mixed in a high speed stirring homogenizer, and the mixture was maintained at 140° C. for 5 days in an autoclave while stirring. After cooling, the reaction product was filtered, washed with water, dried, and calcined in the same manner as described for the catalyst preparation in Example 1. The product was ion-exchanged in an ammonium chloride aqueous solution, filtered, washed with water, dried, and calcined. Titanium was incorporated in the catalyst precursor thus obtained in the same manner as in Example 1-(3), and the resulting product was calcined at 400° C. for 2 hours in an air stream to produce Catalyst 24.

Catalyst 24 was found to have an $SiO_2/Al_2O_3$ molar ratio of 58 as determined by X-ray fluorometric analysis and a ratio of external surface acid sites to total acid sites of 0.14 as determined by the pulse adsorption method.

Hydration reaction was carried out under the same conditions as described in Example 1, except using Catalyst 24 as obtained above, a reaction temperature of 100° C. and a reaction time of 1 hour. The resulting oil phase was analyzed and found to have a cyclohexanol concentration of 16.8 wt%.

EXAMPLE 16

Hydration reaction was carried out under the same conditions as in Example 1 except for using 30 g of cyclopentene as a cyclic olefin and a reaction temperature of 100° C. The resulting oil phase was analyzed and found to have a cyclopentanol content of 1.2 wt%, with no other products being detected.

EXAMPLE 17

Hydration reaction was carried out under the same conditions as in Example 16 except for using 20 g of cyclooctene as a cyclic olefin, a reaction temperature of 140° C. and a reaction time of 80 minutes. The oil phase of the resulting reaction mixture was analyzed and found to have a cyclooctanol concentration of 1.8 wt%, and no other products were detected.

EXAMPLE 18

In a 100 ml-volume stirring autoclave were charged a mixture of 30 g of water and an acid as shown in Table 6 and 10 g of Catalyst 2. After displacing the air in the reaction system with nitrogen, the mixture was reacted at 120° C. for 15 minutes while stirring. After the reaction, the reaction product in oil phase was analyzed by gas chromatography. The results obtained, the kind of the acid used and the acid concentration in its aqueous solution are shown in Table 6 below.

TABLE 6

| Example No. | Acid | Acid Concentration (mol/l) | Cyclohexanol Concentration in Oil Phase (wt %) |
|---|---|---|---|
| 18-A | concentrated sulfuric acid | 0.10 | 13.8 |
| 18-B | concentrated nitric acid | 0.10 | 13.5 |
| 18-C | dodecamolybdophosphoric acid | 0.15 | 12.9 |
| 18-D | aluminum chloride hexahydrate | 0.20 | 13.0 |
| 18-E | boron trifluoride | 0.24 | 12.9 |
| 18-F | titanium tetrachloride | 0.20 | 13.5 |
| 18-G | copper (II) chloride | 0.60 | 12.8 |
| 18-H | chromium (III) chloride hexahydrate | 0.50 | 12.7 |
| 18-I | iron (III) nitrate nonahydrate | 0.54 | 13.1 |
| 18-J | ruthenium (III) chloride hydrate | 0.50 | 12.8 |
| 18-K | cobalt (II) nitrate hexahydrate | 0.52 | 12.7 |
| 18-L | nickel (II) nitrate hexahydrate | 0.50 | 12.7 |
| 18-M | lanthanum (III) nitrate hexahydrate | 0.55 | 13.1 |
| 18-N | thorium (IV) nitrate | 0.50 | 13.4 |
| 18-O | acetic acid | 1.7 | 12.9 |
| 18-P | trifluoroacetic acid | 0.45 | 13.1 |
| 18-Q | p-toluenesulfonic acid | 0.50 | 13.2 |

COMPARATIVE EXAMPLE 4

Hydration reaction was carried out in the same manner as in Example 18-A, except that no catalyst was used. As a result, the cyclohexanol concentration in the oil phase of the resulting reaction mixture was below the detection limit.

EXAMPLE 19

Hydration reaction was carried out under the same conditions as described in Example 18-A, except using Catalyst 18 and a reaction time of 80 minutes. The oil phase of the resulting reaction mixture was found to have a cyclohexanol concentration of 8.4 wt% and to contain 0.06 wt% of dicyclohexyl ether and 0.04 wt% of a cyclohexene dimer as by-products.

EXAMPLE 20

Hydration reaction was carried out under the same conditions as in Example 18-A, except using Catalyst 24 and a reaction time of 12 minutes. The cyclohexanol concentration in the oil phase was 15.4 wt%.

EXAMPLE 21

A mixture of 10 g (0.068 mol) of adipic acid and 30 g of water, 15 g of Catalyst 24 and 15 g of cyclohexene were place in a 100 ml-volume stirring autoclave. After displacing the air in the reaction system with nitrogen, the mixture was reacted at 120° C. for 12 minutes while stirring. The oil phase of the resulting reaction mixture was sampled while hot and analyzed to find that the cyclohexanol concentration was 16.7 wt%.

EXAMPLE 22

Hydration reaction was carried out under the same conditions as in Example 21 except for using 25 g of water, 15 g (0.11 mol) of glutaric acid in place of the adipic acid and a reaction time of 15 minutes. The oil phase of the resulting reaction mixture was found to have a cyclohexanol concentration of 16.1 wt%.

EXAMPLE 23

Hydration reaction was carried out under the same conditions as in Example 22 except for using succinic acid in place of the glutaric acid. The oil phase of the resulting reaction mixture was found to have a cyclohexanol concentration of 16.4 wt%.

EXAMPLE 24

(1) In 700 g of water was dissolved 1,450 g of sodium silicate (water glass No. 3) to prepare Solution A. In 400 g of water were dissolved 104 g of aluminum sulfate and 35 g of concentrated sulfuric acid to prepare Solution B. In 800 g of water was dissolved 170 g of 1,3-dimethylurea to prepare Solution C. Solutions A, B and C were mixed in a homogenizer with stirring. The resulting aqueous gel was placed in a 5-liter stainless steel-made autoclave equipped with a stirrer and heated at 160° C. for 20 hours while stirring at 1.5 m/sec. The thus precipitated crystalline aluminosilicate was separated by centrifugation, washed with water and dried at 120° C. for 4 hours and then calcined at 550° C. for 5 hours in an air stream. The solid was subjected to cation-exchange three times with a 2M aqueous solution of ammonium chloride, washed with water, filtered, dried, and calcined at 400° C. for 2 hours to obtain a proton-exchanged crystalline aluminosilicate (Precursor D). The above-described procedure were repeated five times.

(2) To a mixture of 9.5 g of titanium tetrachloride and 2.5 liter of water was added 250 g of Precursor D, and the mixture was stirred at room temperature for 8 hours. The mixture was washed with water and filtered. The solid product was dried at 80° C. in a nitrogen atmosphere (Catalyst 25).

(3) Catalyst 25 as prepared above was calcined at 400° C. for 2 hours (Catalyst 26).

(4) Catalyst 26 as prepared above was heated at 400° C. in a hydrogen stream (Catalyst 27).

The titanium content and $SiO_2/Al_2O_3$ molar ratio as determined by X-ray fluorometric analysis and the ratio of external surface acid sites to total acid sites as determined by the pulse adsorption method for each of the above-described catalysts and precursor are shown in Table 7.

Ten grams each of the above prepared catalysts, 30 g of water and 15 g of cyclohexene were charged in a 100 ml-volume stirring type autoclave and allowed to react at 100° C. for 2 hours while stirring. After the reaction, the product was analyzed by gas chromatography to obtain the results as shown in Table 7. The product was found to solely comprise cyclohexanol, and no other products were detected.

COMPARATIVE EXAMPLE 5

A mixture of 32 g of aluminum sulfate, 325 g of sodium chloride, 92.5 g of concentrated sulfuric acid, 137 g of tetrapropylammonium bromide and 1,895 g of water was added to a mixture of 1,110 g of Q-brand sodium silicate and 1,385 g of water, and the mixture was mixed in a homogenizer. The resulting aqueous gel was charged in an autoclave and heated at 160° C. for 70 hours while stirring at 1.4 m/sec. The resulting crystalline aluminosilicate was converted to a proton-exchanged crystalline aluminosilicate in the same manner as described in Example 24 (Catalyst 28).

Hydration reaction was carried out in the same manner as in Example 24 but using Catalyst 28 as prepared above. The physical properties and results of the hydration reaction are shown in Table 7.

COMPARATIVE EXAMPLE 6

To 150 g of Q-brand sodium silicate was added 180 g of a 10% aqueous solution of tetrapropylammonium hydroxide, and 4 g of aluminum nitrate [$Al(SO_3)_3.9-H_2O$] and 40 g of water were further added thereto, followed by stirring for 10 minutes. Thereafter, concentrated nitric acid was added dropwise to the resulting solution while vigorously stirring so as to adjust to a pH of 10 to 10.5 to obtain a homogeneous gel. The gel was placed in a 1 liter-volume autoclave equipped with a stirrer, and stirred at 180° C. for 24 hours. The resulting product was washed with a sufficient amount of deionized water followed by drying at 120° C. for 10 hours. The product (Catalyst 29) was identified as ZSM-5 zeolite by X-ray diffractometry.

Hydration reaction was carried out in the same manner as in Example 24 but using Catalyst 29 as above prepared. The physical properties of the catalyst and results of the hydration reaction are shown in Table 7.

EXAMPLE 25

In 81 g of water was dissolved 166 g of sodium silicate (water glass No. 3) to prepare Solution A. In 46 g of water were dissolved 12 g of aluminum sulfate and 2.8 g of concentrated sulfuric acid to prepare Solution B. In 92 g of water was dissolved 26.2 g of 1,3-diethylurea to prepare solution C. Solutions A, B and C were mixed in the same manner as in Example 24, and the mixture was placed in a 500 ml-volume stainless steel-made autoclave and heated at 160° C. for 20 hours while stirring at 0.5 m/sec. The resulting crystalline aluminosilicate was converted to a proton-exchanged crystalline aluminosilicate in the same manner as described in Example 24. Titanium was incorporated in the resulting product in the same manner as in Example 24-(2) (Catalyst 30).

Hydration reaction was carried out in the same manner as in Example 24 but using Catalyst 30 as prepared above. The physical properties of the catayst and results of the hydration reaction are shown in Table 7.

EXAMPLE 26

In 120 g of water was dissolved 128 g of sodium silicate (water glass No. 3) to prepare Solution A. In 40 g of water were dissolved 3.9 g of aluminum sulfate and 4 g of concentrated sulfuric acid to prepare Solution B. In 80 g of water was dissolved 17 g of 1,3-dimethylthiourea to prepare Solution C. Solutions A, B and C were mixed in the same manner as in Example 24, and the mixture was charged in a 500 ml-volume stainless steel-made autoclave and heated at 110° C. for 72 hours while stirring at 1.5 m/sec and then at 160° C. for 10 hours while stirring at the same speed. The resulting crystalline aluminosilicate was converted to a proton-exchanged crystalline aluminosilicate in the same manner as in Example 24. Titanium was incorporated to the product in the same manner as in Example 24-(2) (Catalyst 31).

Hydration reaction was carried out in the same manner as in Example 24 but using Catalyst 31 as prepared above. The physical properties of the catalyst and results of the hydration reaction are shown in Table 7.

EXAMPLE 27

Twenty grams of Precursor D as prepared in Example 24 was added to a mixture of 1.7 g of zirconium nitrate tetrahydrate and 200 ml of water, and the mixture was stirred at room temperature for 8 hours. The mixture thus treated was washed with water and filtered. The solid product was dried and then calcined at 400° C. for 2 hours in an air stream (Catalyst 32).

Hydration reaction was carried out in the same manner as in Example 24 but using Catalyst 32 as prepared above. The physical properties of the catalyst and results of the hydration reaction are shown in Table 7.

EXAMPLE 28

Catalyst 33 was prepared in the same manner as in Example 27 but using 3.70 g of hafnium sulfate in place of zirconium nitrate.

Hydration reaction was carried out in the same manner as in Example 24 but using Catalyst 33 as above prepared. The physical properties of the catalyst and results of the hydration reaction are shown in Table 7.

EXAMPLE 29

Catalyst 34 was prepared in the same manner as in Example 27 except for using 1.4 g of thorium (IV) nitrate in place of zirconium nitrate.

Hydration reaction was carried out in the same manner as in Example 24 but using Catalyst 34. The physical properties of the catalyst and results of the hydration reaction are shown in Table 7.

EXAMPLE 30

Catalyst 35 was prepared in the same manner as in Example 27 except for using 0.82 g of molybdenum (V) chloride in place of zirconium nitrate.

Hydration reaction was carried out under the same conditions as in Example 24 but using Catalyst 35 as above prepared. The physical properties of the catalyst and results of the hydration reaction are shown in Table 7.

EXAMPLE 31

Catalyst 36 was prepared in the same manner as in Example 27 except for using 1.0 g of tungstic acid in place of zirconium nitrate.

Hydration reaction was carried out under the same conditions as in Example 24 but using Catalyst 36 as above prepared. The physical properties of the catalyst and results of the hydration reaction are shown in Table 7.

EXAMPLE 32

Catalyst 37 was prepared in the same manner as described in Example 27 except for using 1.0 g of chromium (I) chloride hexahydrate in place of zirconium nitrate.

Hydration reaction was carried out under the same conditions as in Example 24 but using Catalyst 37 as above prepared. The physical properties of the catalyst and results of the hydration reaction are shown in Table 7.

TABLE 7

| Example No. | Catalyst | Compound Used in Preparation of Catalyst | Element Contained and Content (mol/Kg) | | Silica/Alumina Molar Ratio in Catalyst | Ratio of External Surface Acid Sites/ Total Acid Sites of Catalyst | Cyclohexanol Concentration (wt %) in Oil Phase After Hydration Reaction |
|---|---|---|---|---|---|---|---|
| 24 | 25 | 1,3-dimethylurea | Ti | 0.11 | 28 | 0.24 | 18.1 |
| 24 | 26 | 1,3-dimethylurea | Ti | 0.11 | 29 | 0.25 | 18.7 |
| 24 | 27 | 1,3-dimethylurea | Ti | 0.11 | 28 | 0.25 | 17.7 |
| Comparative Example 5 | 28 | tetrapropylammonium bromide | — | — | 58 | 0.05 | 5.2 |
| Comparative Example 6 | 29 | tetrapropylammonium hydroxide | — | — | 60 | 0.02 | 2.8 |
| 25 | 30 | 1,3-diethylurea | Ti | 0.10 | 29 | 0.21 | 18.1 |
| 26 | 31 | 1,3-dimethylthiourea | Ti | 0.11 | 30 | 0.26 | 17.3 |
| 27 | 32 | 1,3-dimethylurea | Zr | 0.16 | 29 | 0.24 | 18.5 |
| 28 | 33 | 1,3-dimethylurea | Hf | 0.14 | 28 | 0.24 | 18.2 |

TABLE 7-continued

| Example No. | Catalyst | Compound Used in Preparation of Catalyst | Element Contained and Content (mol/Kg) | | Silica/Alumina Molar Ratio in Catalyst | Ratio of External Surface Acid Sites/ Total Acid Sites of Catalyst | Cyclohexanol Concentration (wt %) in Oil Phase After Hydration Reaction |
|---|---|---|---|---|---|---|---|
| 29 | 34 | 1,3-dimethylurea | Th | 0.12 | 28 | 0.23 | 16.9 |
| 30 | 35 | 1,3-dimethylurea | Mo | 0.09 | 30 | 0.25 | 17.7 |
| 31 | 36 | 1,3-dimethylurea | W  | 0.13 | 28 | 0.24 | 17.5 |
| 32 | 37 | 1,3-dimethylurea | Cr | 0.21 | 29 | 0.25 | 18.1 |

EXAMPLE 33

Hydration reaction of cyclohexene was carried out using a continuous flow system reaction apparatus as shown in the figure as follows.

In 500 ml-volume stainless steel-made autoclave 3 equipped with a stirrer were charged 40 g of the catalyst 26 obtained in Example 24 and 120 g of water, and the system was replaced with nitrogen gas. The mixture was stirred at 500 rpm while elevating the temperature to 115° C. Cyclohexene was fed to the reactor through supply pipe 1 at a rate of 120 g/hr, and water was fed thereto through supply pipe 2 at such a feeding rate that the liquid level be maintained constant. The reaction mixture overflowing from the reactor was introduced in liquid-liquid separator 5 through pipe 4. The separated oil phase was withdrawn from the system through discharge pipe 6, with the catalyst-containing aqueous phase being recycled to reactor 3 through recycle pipe 7. The cyclohexanol concentrations of the oil phase discharged after 3 hours and 240 hours from the start of feeding cyclohexene were found to be 11.0% by weight and 10.8% by weight, respectively, and no other products were detected.

COMPARATIVE EXAMPLE 7

Hydration reaction of cyclohexene was carried out in the same manner as in Example 33 but using the catalyst as prepared in Comparative Example 5.

The oil phase discharged after 3 hours and 240 hours from the start of feeding cyclohexene was found to have cyclohexanol concentrations of 3.2% by weight and 1.3% by weight, respectively, and 2.0% by weight of methylcyclopentenes were detected as by-products in the oil phase after 240 hours.

EXAMPLE 34

A mixture of 30 g of water and an acid as shown in Table 8, 15 g of cyclohexene and 10 g of Catalyst 26 were charged in a 100 ml-volume stirring type autoclave. After displacing the atmosphere in the system with nitrogen gas, the mixture was reacted at 100° C. for 2 hours with stirring. After the reaction, the product was analyzed. The results obtained, the kind of the acid used and the acid concentration in its aqueous solution are shown in Table 8 below.

TABLE 8

| Example No. | | Acid Concentration (mol/l) | Cyclohexanol Concentration in Oil Phase (wt %) |
|---|---|---|---|
| 34-A | concentrated sulfuric acid | 0.10 | 20.0 |
| 34-B | concentrated nitric acid | 0.10 | 19.5 |
| 34-C | dodecamolybdophosphoric acid | 0.15 | 19.2 |
| 34-D | aluminum chloride hexahydrate | 0.20 | 19.6 |
| 34-E | boron trifluoride | 0.25 | 19.2 |
| 34-F | titanium tetrachloride | 0.20 | 20.0 |
| 34-G | copper (II) chloride | 0.60 | 19.1 |
| 34-H | chromium (III) chloride hexahydrate | 0.50 | 18.9 |
| 34-I | iron (III) nitrate nonahydrate | 0.55 | 19.0 |
| 34-J | acetic acid | 1.7 | 19.2 |
| 34-K | trifluoroacetic acid | 0.45 | 19.7 |
| 34-L | p-toluenesulfonic acid | 0.50 | 19.5 |

While the invention has been described in detail and with reference to specific embodiments thereof, it will be apparent to one skilled in the art that various changes and modifications can be made therein without departing from the spirit and scope thereof.

What is claimed is:

1. A process for producing a cyclic alcohol by catalytic hydration of a cyclic olefin with water, comprising using as a catalyst a crystalline aluminosilicate containing at least one member selected from the group consisting of titanium, zirconium, hafnium, chromium, molybdenum, tungsten, and thorium; wherein said catalytic hydration is carried out at a temperature of from about 50° to 250° C.

2. A process as in claim 1, wherein said catalyst is a crystalline aluminosilicate containing at least one member selected from the group consisting of titanium, zirconium, hafnium, and throium.

3. A process as in claim 1, wherein said catalytic hydration is conducted in the presence of an acid in the form of an aqueous solution.

4. A process as in claim 3, wherein said acid is an inorganic compound which acts as a Bronsted acid or a Lewis acid.

5. A process as in claim 3, wherein said acid is an organic carboxylic acid or an organic sulfonic acid.

6. A process as in claim 1, wherein said crystalline aluminosilicate has a molar ratio of silica to aluminum of 10/1 or more.

7. A process as in claim 1, wherein said crystalline aluminosilicate has a population ratio of external surface acid sites to total acid sites of 0.02/1 or more.

8. A process as in claim 1, wherein said cyclic olefin is cyclopentene, cyclohexene, methylcyclopentenes, methylcyclohexenes, cyclooctene, or cyclododecene.

9. A process as in claim 8, wherein said cyclic olefin is cyclohexene.

10. A process as in claim 2, wherein said cyclic olefin is cyclohexene.

11. A process as in claim 3, wherein said cyclic olefin is cyclohexene.

12. A process as in claim 6, wherein said cyclic olefin is cyclohexene.

13. A process as in claim 7, wherein said cyclic olefin is cyclohexene.

14. A process as in claim 1, wherein the total amount of titanium, zirconium, hafnium, chromium, molybdenum, tungsten, and thorium present in the crystalline aluminosilicate is in the range of from about 0.002 to about 5.0 moles per kilogram of the crystalline aluminosilicate.

15. A process as in claim 14, wherein said total amount of titanium, zirconium, hafnium, chromium, molybdenum, tungsten, and thorium present in the crystalline aluminosilicate is in the range of from 0.004 to 2.0 moles per kilogram of the crystalline aluminosilicate.

16. A process as in claim 15, wherein said total amount of titanium, zirconium, hafnium, chromium, molybdenum, tungsten, and throium present in the crystalline aluminosilicate is in the range of from 0.01 to 1.0 mole per kilogram of the crystalline aluminosilicate.

17. A process as in claim 1, wherein said crystalline aluminosilicate comprises mordenite, faujasite, pentasil type zeolite, erionite, ferrierite, or offretite.

18. A process as in claim 17, wherein said cyclic olefin is cyclohexene.

19. A process as in claim 17, wherein said crystalline aluminosilicate comprises mordenite or pentasil type zeolite.

20. A process as in claim 19, wherein said cyclic olefin is cyclohexene.

21. A process as in claim 19, wherein said crystalline aluminosilicate is a pentasil type zeolite prepared by templating at least one compound selected from the group consisting of a lower alkylurea and a lower alkylthiourea.

22. A process as in claim 21, wherein said cyclic olefin is cyclohexene.

23. A process as in claim 1, wherein said crystalline aluminosilicate is prepared by immersing a crystalline aluminosilicate in an aqueous solution of a compound of at least one member selected from the group consisting of titanium, zirconium, hafnium, chromium, molybdenum, tungsten, and thorium.

24. A process as in claim 1, wherein said crystalline aluminosilicate is prepared by evaporating a mixture of a crystalline aluminosilicate and a compound of at least one member selected from the group consisting of titanium, zirconium, hafnium, chromium, molybdenum, tungsten, and thorium to dryness.

25. A process as in claim 3, wherein said acid has a concentration of from 0.001 to 5 mol/l in the aqueous solution thereof.

26. A process as in claim 25, wherein said acid has a concentration of from 0.005 to 2 mol/l in the aqueous solution thereof.

27. A process as in claim 4, wherein said inorganic compound comprises at least one member selected from the group consisting of sulfuric acid, nitric acid, hydrochloric acid, molybdic acid, tungstic acid, and heteropoly acid.

28. A process as in claim 4, wherein said inorganic compound comprises at least one member selected from the group consisting of a halide of an aluminum family element, a halide of a transition metal, a sulfate of a transition metal, and a transition metal complex.

29. A process as in claim 5, wherein said organic carboxylic acid comprises at least one member selected from the group consisting of formic acid, acetic acid, propionic acid, trifluoroacetic acid, succinic acid, glutaric acid, and adipic acid.

30. A process as in claim 5, wherein said organic sulfonic acid comprises at least one member selected from the group consisting of methanesulfonic acid, trifluoromethanesulfonic acid, benzenesulfonic acid, and p-toluenesulfonic acid.

31. A process as in claim 1, wherein said catalytic hydration is carried out at a temperature of from 60° to 200° C.

32. A process as in claim 3, wherein said crystalline aluminosilicate has a molar ratio of silica to alumina of 10/1 or more.

33. A process as in claim 3, wherein said crystalline aluminosilicate has a population ratio of external surface acid sites to total acid sites of 0.02/1 or more.

34. A process as in claim 3, wherein said cyclic olefin is cyclopentene, cyclohexene, methylcyclopentenes, methylcyclohexenes, cyclooctene or cyclododecene.

35. A process as in claim 34, wherein said cyclic olefin is cyclohexene.

36. A process as in claim 3, wherein the total amount of titanium, zirconium, hafnium, chromium, molybdenum, tungsten, and thorium present in the crystalline aluminosilicate is in the range of from about 0.002 to about 5.0 moles per kilogram of the crystalline aluminosilicate.

37. A process as in claim 3, wherein said crystalline aluminosilicate comprises mordenite, faujasite, pentasil type zeolite, erionite, ferrierite, or offretite.

38. A process as in claim 3, wherein said crystalline aluminosilicate is prepared by immersing a crystalline aluminosilicate in an aqueous solution of a compound of at least one member selected from the group consisting of titanium, zirconium, hafnium, chromium, molybdenum, tungsten, and thorium.

39. A process as in claim 3, wherein said crystalline aluminosilicate is prepared by evaporating a mixture of a crystalline aluminosilicate and a compound of at least one member selected from the group consisting of titanium, zirconium, hafnium, chromium, molybdenum, tungsten, and thorium to dryness.

* * * * *